(12) United States Patent
Bara

(10) Patent No.: US 6,432,391 B1
(45) Date of Patent: Aug. 13, 2002

(54) TRANSPARENT SCENTED SOLID COSMETIC COMPOSITION

(75) Inventor: Isabelle Bara, Paris (FR)

(73) Assignee: L'Oréal S.A. (FR)

( * ) Notice: Subject to any disclaimer, the term of this patent is extended or adjusted under 35 U.S.C. 154(b) by 0 days.

(21) Appl. No.: 09/899,909

(22) Filed: Jul. 9, 2001

Related U.S. Application Data
(60) Provisional application No. 60/262,636, filed on Jan. 22, 2001.

(30) Foreign Application Priority Data

Jul. 7, 2000 (FR) .............................. 00 08913

(51) Int. Cl.$^7$ ............................ A61K 7/32; A61K 7/00; A61K 31/74
(52) U.S. Cl. .................. 424/65; 424/78.02; 424/78.08; 424/400; 424/401
(58) Field of Search ................. 424/65, 78.02, 424/78.08, 400, 401

(56) References Cited

U.S. PATENT DOCUMENTS

| | | |
|---|---|---|
| 3,148,125 A | 9/1964 | Strianse et al. |
| 3,645,705 A | 2/1972 | Miller et al. |
| 4,552,693 A | 11/1985 | Hussain et al. |
| 5,500,209 A | 3/1996 | Ross et al. |
| 5,603,925 A | 2/1997 | Ross et al. |
| 5,783,657 A | 7/1998 | Pavlin et al. |

FOREIGN PATENT DOCUMENTS

| | | |
|---|---|---|
| EP | 0 797 976 | 10/1997 |
| GB | 1 273 004 | 5/1972 |
| GB | 1 444 204 | 7/1976 |

*Primary Examiner*—Shelley A. Dodson
(74) *Attorney, Agent, or Firm*—Finnegan, Henderson, Farabow, Garrett & Dunner, L.L.P.

(57) ABSTRACT

A transparent and optionally colored solid cosmetic composition comprising, in a physiologically acceptable medium, at least one odorous substance in an amount effective for scenting a cosmetic substrate and a liquid fatty phase comprising at least one polymer, chosen from: (1) polymers with a weight-average molecular mass ranging from 1,000 to 30,000, comprising a) a polymer backbone having hydrocarbonaceous repeat units provided with at least one heteroatom and b) at least one fatty chain chosen from pendant and end fatty chains, where the at least one fatty chain is optionally functionalised; comprises from 12 to 120 carbon atoms; and is bonded to at least one of the repeat units; and (2) polyamides with a weight-average molecular mass ranging from 1,000 to 30,000, comprising a) a polymer backbone comprising amide repeat units and b) optionally at least one fatty chain chosen from pendant and end fatty chains, where the at least one fatty chain is optionally functionalised; comprises from 12 to 120 carbon atoms; and is bonded to at least one of the amide units.

63 Claims, No Drawings

TRANSPARENT SCENTED SOLID COSMETIC COMPOSITION

The benefits of priority are claimed from French Patent Application No. 0008913, filed Jul. 7, 2000, and from U.S. Provisional Application No. 60/262,636, filed Jan. 22, 2001.

The present invention relates to a product comprising a solid, transparent and optionally colored cosmetic composition which comprises at least one odorous substance (such as, for example, fragrances and/or aromas), which can be used to scent, for example, at least one cosmetic substrate, including, for example, cosmetic substrates chosen from human skin, keratinous substances, scalps, and lips, and which comprises a liquid fatty phase gelled by a specific polymer. The product can be provided in various forms such as, for example, cast products and sticks. The use of the product, which can include for example, cosmetic uses, includes the application of the composition, which can result in a controlled and/or enhanced persistence of the at least one odorous substance.

A fragrance can be a combination of various odorous substances which evaporate at different rates and/or during different periods. Fragrance can exhibit what is known as a "top note," which is the odour which first diffuses when the fragrance is applied or when the receptacle comprising it is opened, a "heart note" or "body note," which corresponds to the complete fragrance (emission for several hours after the "top note"), and a "base note," which is the most persistent odour (emission for several hours after the "heart note"). The persistence of the base note corresponds to the persistence of the fragrance.

From time immemorial, human beings have attempted to wear perfume and to scent the objects which surround them or the places in which they are found, both to mask strong and/or unpleasant smells and to give a pleasant smell.

Fragrance can be incorporated in a number of products and compositions, such as, for example, cosmetic and dermatological products and compositions. However, depending upon the nature of the products or compositions, it can be difficult to incorporate a fragrance and it can be difficult to retain the desired olfactory effects.

There exist scenting products intended to scent at least one of the skin and the hair. Scenting products are typically presented in the form of a liquid, the fragrance of which is dissolved with alcohol (ethanol, for example). Alcohol-free solid fragrances, presented in the form of, for example, dishes, can offer the consumer a new way of wearing perfume with advantages such as, for example, being less irritating and being nonflammable in comparison to alcohol based products. Other advantages of the solid form can include the ability to apply scent at a specific location, which a spray does not always make possible, and to prevent possible splashing of the fragrance.

The scenting "solids" include anhydrous forms, rich in "fatty substances" (or "scenting balm") that can help in providing good solubility to the fragrances, and forms rich in powder, such as compressed powders similar to the compact powders used in make-up. These solid forms can be opaque, because, for example, they are prepared with waxes with a crystal lattice that introduces a degree of opaqueness or they comprise nontransparent powders.

Transparency or translucency can be a desired and valued effect and can correspond to trends in other sectors, such as textiles or design. The phenomenon of transparency can also make possible incorporation inside the solid of objects which are visible to the naked eye, such as particulate components (for example, immiscible components such as glitter, granules, spheres, and the like). Transparent products can be superimposed on colored "conventional" make-up products, such as, for example lipsticks, without modifying the original color thereof in order to, for example, convey a pleasant smell to the lips.

There is a need for scenting products, including, for example, cosmetic products, which do not exhibit one or more of above-identified and/or other disadvantages. For example, there is a need for transparent and optionally colored scenting products, for giving the consumer a new visual image of a scented composition, which can enhance the persistence of the fragrance on, for example, a surface or object, such as keratinous substances, without this fragrance decomposing, including, for example, decomposing on contact with other constituents of the composition. The surface or object, such as keratinous substances, to which such a composition may be applied include, for example, the skin, the lips, the superficial body growths, and keratinous substances.

To meet these and/or other needs, it is, however, difficult to prepare a solid composition (that is, a composition that does not flow under its own weight) comprising a high concentration of at least one odorous substance (such as, for example, a fragrance and/or an aroma) without affecting the transparency of the solid composition, since the incorporation of a fairly large amount of at least one odorous substance can result in an opaque product.

Surprisingly, the inventor has discovered that specific polymers can make it possible to gel oils and to obtain cosmetic products comprising transparent solids, and to incorporate high levels of at least one odorous substance without harming the transparency of the product. The polymer may be chosen from at least one polymer comprising a polymer backbone having repeating units with heteroatoms and at least one of a pendant fatty chain and an end fatty chain, and at least one polyamide comprising a polymer backbone having amide repeat units and optionally at least one of a pendant fatty chain and an end fatty chain.

One embodiment of the present invention is a product, for example a scenting product, comprising a transparent, anhydrous, solid cosmetic composition comprising a physiologically acceptable medium, where the physiologically acceptable medium comprises at least one odorous substance in an amount of at least 2% by weight with respect to a total weight of the composition; and a liquid fatty phase comprising at least one polymer, where the at least one polymer has a weight-average molecular mass ranging from 1,000 to 30,000, and comprises a) a polymer backbone comprising hydrocarbonaceous repeat units comprising at least one heteroatom and b) at least one fatty chain chosen from pendant and end fatty chains, where the at least one fatty chain is optionally functionalised; comprises from 12 to 120 carbon atoms; and is bonded to at least one of the hydrocarbonaceous repeat units.

Another embodiment of the present invention is a product, for example a scenting product, comprising a transparent, anhydrous, solid cosmetic composition comprising a physiologically acceptable medium, where the physiologically acceptable medium comprises at least one odorous substance in an amount of at least 2% by weight; and a liquid fatty phase comprising at least one polyamide, wherein the at least one polyamide has a weight-average molecular mass ranging from 1,000 to 30,000, and comprises a) a polymer backbone comprising amide repeat units and b) optionally at least one fatty chain chosen from pendant and end fatty chains, wherein the at least one fatty chain is optionally functionalised; comprises from 12 to 120 carbon atoms; and is bonded to at least one of the amide units.

According to certain embodiments, the amount of the at least one odorous substance in the composition of the invention can range from 2 to 15%, for example from 3 to 12%, such as, for further example, from 4 to 10% by weight with respect to the total weight of the composition.

The term "physiologically acceptable medium" is understood to mean, in the composition of the invention, a nontoxic medium capable of being applied to at least one of the skin (such as, for example, the inside of the eyelids), the lips, the nails, and the hair of human beings.

The term "solid composition" is understood to mean, within the meaning of the present invention, any malleable or nonmalleable composition which does not flow under its own weight and exhibits a hardness with a strength ranging from 5 to 600 g (gram), for example from 10 to 450 g, such as, for further example, from 50 to 450 g. This hardness can be measured according to a method of penetration of a probe into the composition, for example by using a texture analyzer (for example, TA-XT2 from Rheó) equipped with a stainless steel cylinder with a height of 2.5 cm and a diameter of 2 mm. The hardness measurement is carried out at approximately 20° C. at a center of 5 samples of the composition. The cylinder is introduced into each sample at a pre-rate of 2 mm/s, then at a rate of 1 mm/s and finally at a post rate of 2 mm/s, the total displacement being 2 mm. The area of the sample under test is at least ten times greater than the diameter of the probe, and its thickness is at least 1 cm. The value recorded of the hardness is that of the maximum peak measured according to this method.

According to certain embodiments, the product of the invention can be applied directly to a substrate, that is to say it does not necessarily need to be wetted in order to be applied to the substrate such as, for example, the skin. The term "substrate" is understood to mean, for the product according to the present invention, any surface on which a topical application can be carried out, including, for example, cosmetic substrates, which include, for example, skin, keratinous fibers, such as for example eyelashes and hair, the scalp, and mucous membranes, such as, for example, lips.

According to certain embodiments, the composition according to the invention can be a transparent composition. The term "transparent composition" is understood to mean, within the meaning of the present invention, a transparent to translucent composition, that is to say such that it has a turbidity value of less than 800 NTU, for example less than 600 NTU. NTUs (Nephelometric Turbidity Units) are the units for the measurement of turbidity of a composition. The turbidity measurement is carried out, for example, with a model 2100P turbidimeter from Hach Compagny, the tubes used for the measurement being referenced AR397A cat 24347-06. The measurements are carried out at ambient temperature (from 20° C. to 25°C.). The value of the turbidity depends on the transparency of the product and also on its color, if it comprises a colorant. Thus, a blue transparent composition can have a turbidity value ranging up to 750 NTU, whereas a red transparent composition can have a turbidity value ranging up to 200 NTU.

The at least one polymer used in the compositions according to the invention can make it possible to obtain a solid composition that is at least one of malleable and nonmalleable, having a strength and a stiffness which are satisfactory for leaving a layer on the skin (or other substrate, such as, for example, a cosmetic substrate) satisfactory for application of the at least one odorous substance. According to certain embodiments, the product of the invention can be provided in the form of at least one of a transparent stick and a transparent cast product in at least one of a dish and a pot.

The term "odorous substance," as used in the present application, is understood to mean any fragrance and/or any aroma capable of giving off an odour.

The term "liquid fatty phase" is understood to mean, within the meaning of the present invention, a fatty phase, liquid at ambient temperature (approximately 25° C.) and an atmospheric pressure (approximately 760 mm of Hg), comprising at least one fatty substance which is liquid at ambient temperature, also known as oils, and which, if there is more than one fatty substance, are compatible with one another.

The liquid fatty phase can be structured by the at least one polymer and this structure (or gelling) of the liquid fatty phase can be varied according to the nature of the at least one polymer used. This structuring (or gelling) of the liquid fatty phase can make possible, for example, a controlled release of the at least one odorous substance (for example, the at least one fragrance), such that the release occurs at least one of during the application to the substrate (such as, for example, the skin) and in a prolonged way over time. The composition of the invention can promote good persistence of the at least one odorous substance, such that the smell of the at least one odorous substance persists for a longer period of time than in the absence of the liquid fatty phase.

According to certain embodiments, the present invention comprises a method of controlling a persistence of at least one odorous substance on a cosmetic substrate comprising incorporating the at least one odorous substance in a cosmetic composition comprising a physiologically acceptable medium comprising at least one polymer in an amount effective for controlling the persistence of the at least one odorous substance, where the at least one polymer has a weight-average molecular mass ranging from 1,000 to 30,000; and comprises a) a polymer backbone comprising hydrocarbonaceous repeat units comprising at least one heteroatom and b) at least one fatty chain chosen from pendant and end fatty chains, where the fatty chains are optionally functionalised, comprise from 12 to 120 carbon atoms, and are bonded to the hydrocarbonaceous repeat units. The composition can be, for example, a cosmetic composition. The method may further comprise applying the composition to a substrate, such as, for example, a cosmetic substrate.

According to certain embodiments, the present invention comprises a method of controlling a persistence of at least one odorous substance on a cosmetic substrate comprising incorporating the at least one odorous substance in a cosmetic composition comprising a physiologically acceptable medium comprising at least one polyamide in an amount effective for controlling the persistence of the at least one odorous substance, where the at least one polyamide has a weight-average molecular mass ranging from 1,000 to 30,000, and comprises a) a polymer backbone comprising amide repeat units and b) optionally at least one fatty chain chosen from pendant and end fatty chains, where the pendant and end fatty chains are optionally functionalized pendant, comprise from 12 to 120 carbon atoms which, and are bonded to the amide units. The composition can be, for example, a cosmetic composition. The method may further comprise applying the composition to a substrate, such as, for example, a cosmetic substrate.

The term "effective amount" is understood to mean with respect to the at least one polymer and the at least one polyamide, in practice, an amount of at least 2%, for example at least 3%, such as, as further example, more than 4%, by weight with respect to the total weight of the composition. The amount of the at least one odorous substance can range, for example, from 2 to 15% by weight, such as, for example, from 3 to 12% by weight, and, as a further example, from 4 to 10%, by weight with respect to the total weight of the composition.

According to certain embodiments, the structuring polymer of the composition of the invention can be a solid which is nondeformable at ambient temperature (25° C.). It can be capable of structuring the composition without rendering it opaque.

The term "polymer" is understood to mean, within the meaning of the present invention, a compound having at least two repeat units.

The term "functionalized chains" is understood to mean, within the meaning of the present invention, an alkyl chain comprising at least one group chosen from functional and reactive groups, for example, at least one group chosen from hydroxyl, ether, oxyalkylene, polyoxyalkylene, carboxyl, amine, halogen, such as fluorinated, and perfluorinated, ester, siloxane, and polysiloxane groups. In addition, it is understood that the hydrogen atoms of at least one fatty chain optionally can be at least partially substituted by at least one fluorine atom. The fatty chains can comprise from 12 to 120 carbon atoms, for example from 12 to 68 carbon atoms.

The terms "hydrocarbonaceous repeat units" and "hydrocarbonaceous repeating units" are understood to mean, within the meaning of the present invention, a unit comprising from 2 to 80 carbon atoms, for example from 2 to 60 carbon atoms, carrying hydrogen atoms and optionally oxygen atoms, which can be linear, branched or cyclic and can be saturated or unsaturated. In addition, these units each can comprise at least one nonpendant heteroatom in the polymer backbone. These heteroatoms can be chosen from nitrogen, sulfur, and phosphorus atoms, optionally in combination with at least one oxygen atom. The units can additionally comprise a polar group of the carbonyl type.

These units with a heteroatom can be chosen from, for example, amide units which form a backbone of the polyamide type or carbamate and/or urea units which form a polyurethane, polyurea and/or polyurea-urethane backbone. According to certain embodiments, these units are chosen from amide units.

According to certain embodiments, the fatty chain can be bonded directly to at least one heteroatom of the polymer backbone.

According to certain embodiments, the polymer optionally can comprise at least one unit, chosen from silicone and oxyalkylenated units, between the hydrocarbonaceous units.

According to certain embodiments, the polymer of the composition of the present invention can comprise the at least one fatty chain in an amount ranging from 40 to 98%, for example from 50 to 95%, of fatty chains with respect to the total number of units with a heteroatom and the at least one fatty chain. The nature and the proportion of the units with a heteroatom can depend on the nature of the liquid fatty phase and can be, for example, similar to the nature of the fatty phase. Thus, without intending to be bound by theory, the more the units with a heteroatom increase in polarity and in proportion in the polymer, which corresponds to the presence of several heteroatoms, the greater the affinity of the polymer for polar oils. On the other hand, the more the units with a heteroatom decrease in polarity, indeed even become nonpolar, or in proportion, the greater the affinity of the polymer for nonpolar oils.

According to certain embodiments, the composition of the present invention does not comprise silicon resin, with siloxysilicate units, or trimethylated silica, in order to, for example, retain comfort properties of the composition.

According to one embodiment of the present invention, the structuring polymer is a polyamide optionally comprising at least one optionally functionalized fatty chain chosen from pendant and end chains. When they are present, the pendant fatty chains can be bonded to at least one of the nitrogen atom of the amide units. The fatty chains of this polyamide can be present in an amount ranging from 40 to 98% of the total number of the amide units and of the fatty chains, for example from 50 to 95%.

Mention may be made, as structuring polymers which can be used in the composition of the invention, of branched polyamides with at least one of pendant and end fatty chains having from 12 to 120 carbon atoms, for example from 12 to 68 carbon atoms, the end fatty chains being bonded to the polyamide backbone via ester groups. These polymers include those disclosed in U.S. Pat. No. 5,783,657 assigned to Union Camp, the description of polymers therein being specifically incorporated by reference. The polymers can be chosen from those according to the following formula (I):

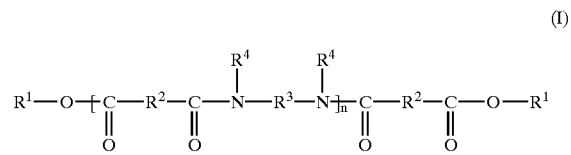

(I)

where n denotes a whole number of amide units, with the proviso that the polymer of formula (I) comprises ester groups in an amount ranging from 10 to 50% of a total number of ester and amide groups; each $R^1$ is, independently, chosen from alkyl and alkenyl groups comprising at least 4 carbon atoms; each $R^2$ is, independently, chosen from $C_4$ to $C_{42}$ hydrocarbonaceous groups, with the proviso that at least 50% of the $R^2$ groups are chosen from $C_{30}$ to $C_{42}$ hydrocarbonaceous group; each $R^3$ is, independently, chosen from organic groups comprising at least 2 carbon atoms, at least one hydrogen atom, and optionally at least one atom chosen from oxygen and nitrogen atoms; and each $R^4$ is, independently, chosen from a hydrogen atom, $C_1$ to $C_{10}$ alkyl groups, and a direct bond to one of $R^3$ and another $R^4$ such that the nitrogen atom to which both $R^3$ and $R^4$ are bonded forms part of a heterocyclic structure defined by $R^4$—N—$R^3$, with the proviso that at least 50% of the $R^4$ groups are chosen from a hydrogen atom.

According to certain embodiments, the ester groups of the formula (I), which can form part of at least one of the end and pendant fatty chains within the meaning of the present invention, can be present in an amount ranging from 15 to 40% of the total number of the ester and amide groups, for example from 20 to 35%. According to certain embodiments, n can represent an integer ranging from 1 to 5. $R^1$ can be chosen from $C_{12}$ to $C_{22}$ alkyl groups, for example from $C_{16}$ to $C_{22}$ alkyl groups. $R^2$ can be chosen from $C_{10}$ to $C_{42}$ hydrocarbonaceous groups (for example alkylene groups) having a structure of one of a polymerized fatty acid and a dimerized fatty acid, the carboxylic acid groups of which have been removed (these groups being used for formation of the amide). According to certain embodiments, at least 50%, for example at least 75%, of the $R^2$ groups are chosen from groups having from 30 to 42 carbon atoms. The other $R^2$ groups can be chosen from $C_4$ to $C_{19}$ groups, for example, $C_4$ to $C_{12}$, hydrogenated groups. According to certain embodiments, $R^3$ can be chosen from $C_2$ to $C_{36}$ hydrocarbonaceous groups, polyoxyalkylenated groups, and a hydrogen atom. For example, $R^3$ can be chosen from $C_2$ to $C_{12}$ hydrocarbonaceous groups. The hydrocarbonaceous groups can be chosen from linear, cyclic, and branched and saturated and unsaturated groups. The alkyl and alkylene groups can be chosen from linear and branched and saturated and unsaturated groups.

According to certain embodiments, the polymer of the composition of the present invention can comprise a weight-average molecular mass ranging from 2,000 to 20,000, for example from 2,000 to 10,000.

According to certain embodiments of the present invention, the structuring of the liquid fatty phase can be obtained using at least one polymer, for example at least one polymer chosen from formula (I). The polymers of formula (I) are generally provided in the form of mixtures of polymers, and these mixtures can be used according to certain embodiments. These mixtures may additionally comprise, among other things, a synthesis product corresponding to a compound of formula (I) where n has the value 0, that is to say a diester, and these mixtures can be used according to certain embodiments.

Mention may be made, by way of example of polymers which can be used in the composition according to the present invention, of the commercial products made and/or sold by Bush Boake Allen under the names UNICLEAR 80 and UNICLEAR 100. They are sold respectively in the form of an 80% (as active material) gel in a mineral oil and a 100% (as active material) gel. They have a softening point of from 88 to 94° C. These commercial products are copolymers of a $C_{36}$ diacid condensed with ethylenediamine, which copolymers are esterified with one of cetylstearyl alcohol and stearyl alcohol, with an average molecular mass ranging approximately from 4,000 to 6,000.

Mention may also be made, as a structuring polymer which can be used in the present invention, of polyamide resins resulting from the condensation of an aliphatic dicarboxylic acid and of a diamine (including, for example, compounds having more than 2 carbonyl groups and 2 amine groups), the carbonyl and amine groups of adjacent individual units being condensed via an amide bond. These polyamide resins can be, for example, those made and/or sold under the trade name VERSAMID® by General Mills, Inc. and Cognis (VERSAMID 930, 744 or 1655) or under the tradename ONAMID®, in particular ONAMID S or C, by Olin Mathieson Chemical Corp. These resins have a weight-average molecular mass ranging from 6,000 to 9,000. For further information on these polyamides, reference may be made to U.S. Pat. Nos. 3,645,705 and 3,148,125, the descriptions of polyamides therein being specifically incorporated herein by reference. For example, according to certain embodiments of the present invention, at least one of VERSAMID® 930 and 744 can be used.

According to certain embodiments, use may also be made of the commercial products made and/or sold under the name CASAMID® (CASAMID 872, 876, 879) by Swan: these polymers are polyamides of fatty acid dimers and of aliphatic diamines.

According to certain embodiments, use may also be made of the polyamides based on dimerized fatty acids made and/or sold by Arizona under the references UNI-REZ (110, 120, 118, 126, 138, 141) and the product made and/or sold under the reference MACROMELT 6212 by Henkel. For further information on these polyamides, reference may be made to U.S. Pat. No. 5,500,209, the description of polyamides therein being specifically incorporated herein by reference.

Of course, mixtures of polymers indicated above can be used.

According to certain embodiments, the structuring polymers of the composition of the present invention can have a softening temperature of greater than 70° C., and, for example, ranging up to 190° C. For example, they can exhibit a softening temperature ranging from 80 to 130° C. These polymers can be, for example, nonwaxy polymers.

According to certain embodiments, the composition can comprise an amount of the at least one polymer, as active material, ranging from 0.5 to 50% by weight, for example from 5 to 40% by weight and, as further example, from 10 to 30% by weight with respect to the total weight of the composition.

Use may be made, in the composition of the present invention, as the at least one odorous substance, of at least one of a fragrance and an aroma of natural or synthetic origin and their mixtures. Mention may be made, as fragrances and aromas of natural origin, of, for example, extracts of flowers (for example, lily, lavender, rose, jasmine, and ylang-ylang), of stems and of leaves (for example patchouli, geranium, and pettigrain), of fruits (for example, coriander, anise, caroway, and juniper), of fruit rinds (for example, bergamot, lemon, and orange), of roots (for example, angelica, celery, cardamon, iris, and sweetflag), of wood (for example, pinewood, sandalwood, lignum vitae, and pink cedar), of grasses and of gramineous plants (for example, tarragon, lemon grass, sage, and thyme), of needles and of branches (for example, spruce, fir, pine, and dwarf pine), and of resins and of balms (for example, galbanum, elemi, benzoin, myrrh, olibanum, and opopanax).

Mention may be made, as odorous substances of synthetic origin, of, for example, compounds comprising at least one of ester, ether, aldehyde, ketone, aromatic alcohol and hydrocarbon groups.

Mention may be made, as esters, of, for example, benzyl acetate, benzyl benzoate, phenoxyethyl isobutyrate, p-tert-butylcyclohexyl acetate, citronellyl acetate, citronellyl formate, geranyl acetate, linalyl acetate, dimethylbenzylcarbonyl acetate, phenylethyl acetate, linalyl benzoate, benzyl formate, ethylmethylphenyl glycinate, alkylcyclohexyl propionate, styralyl propionate, and benzyl salicylate.

Mention may be made, as ethers, of, for example, benzyl ethyl ether.

Mention may be made, as aldehydes, of, for example, linear alkanals comprising from 8 to 18 carbon atoms, citral, citronellal, citronellyloxyacetaldehyde, cyclamen aldehyde, hydroxycitronellal, lilial, and bourgeonal.

Mention may be made, as ketones, of, for example, ionones, for example α-isomethylionone, and methyl cedryl ketone.

Mention may be made, as aromatic alcohol and, for example terpene alcohols, of, for example, anethole, citronellol, eugenol, isoeugenol, geraniol, linalol, phenylethyl alcohol, and terpineol.

Mention may be made, as hydrocarbons of, for example, terpenes. These compounds optionally can be provided in the form of a blend of two or more of these odorous substances.

Furthermore, use may also be made, for example, as the at least one odorous substance, of essential oils, components of aromas, such as, for example, oils of sage, of camomile, of clove, of balm, of mint, of cinnamon leaf, of lime blossom, of juniper, of vetiver, of olibanum, of galbanum, of labolanum, and of lavandin.

Use can be made, as the at least one odorous substance, alone or as a blend, of oil of bergamot, dihydromyrcenol, lilial, lyral, citronellol, phenylethyl alcohol, α-hexylcinnamaldehyde, geraniol, benzylacetone, cyclamen aldehyde, linalol, ambroxan, indol, hedione, sandelice, oils of lemon, mandarin and of orange, allyl amine glycolate, cyclovertal, oil of lavender, oil of sage, β-damascone, oil of geranium, cyclohexyl salicylate, phenylacetic acid, geranyl acetate, benzyl acetate, and rose oxide.

According to certain embodiment of the present invention, a blend of various odorous substances, which generate, in common, a scenting note which is pleasing to the user, can be used.

The liquid fatty phase of the composition can be present, for example, in an amount of at least 20% of the total weight of the composition, for example ranging from 20 to 88.5% by weight, for example from 30 to 85% by weight, and, as a further example, from 40 to 80% by weight with respect to the total weight of the composition.

According to certain embodiments, the liquid fatty phase can comprise at least one oil chosen from polar and nonpolar oils, of different chemical natures, and can be used individually and as mixtures. The oils can be chosen such that they do not harm the transparency of the composition. According to certain embodiments of the present invention, the liquid fatty phase can comprise at least one polar oil and at least one nonpolar oil.

Mention may be made, for example, as polar oils, of:

hydrocarbonaceous vegetable oils with a high content of triglycerides composed of esters of fatty acids and of glycerol, the fatty acids of which can have varied chain lengths, it being possible for these chains to be linear or branched and unsaturated or saturated; these oils include, for example, wheat germ, maize, sunflower, karite, castor, sweet almond, macadamia, apricot, soybean, cottonseeds, alfalfa, poppy, pumpkin seed, sesame, cucumber, avocado, hazelnut, grapeseed, black current seed, evening primrose, millet, barley, quinoa, olive, rye, safflower, candlenut, passionflower and musk rose oils; and triglycerides of caprylic/capric acid, such as, for example, those sold by Stearineries Dubois and those sold under the names MIGLYOL 810, 812 and 818 by Dynamit Nobel;

synthetic esters and ethers, such as, for example, isopropyl myristate, octanoates, decanoates, and ricinoleates of alcohols and of polyalcohols, for example esters of $C_8$–$C_{24}$ fatty acids and of polyols such as, for example glycerol, sorbitan, glucose, and methylglucose, such as, for example sorbitan, glyceryle, glucose, and methylglucose stearates, isostearates, hydroxystearates, and oleates; synthetic oils of formula $R_5COOR_6$ in which $R_5$ is chosen from residues of linear and branched higher fatty acids comprising from 1 to 40, for example from 7 to 19, carbon atoms and $R_6$ is chosen from branched hydrocarbonaceous chains comprising from 1 to 40, for example from 3 to 20, carbon atoms, with the proviso $R_5$ and $R_6$ that together comprise at least 10 carbon atoms, such as, for example, purcellin oil (cetostearyl octanoate) and isononyl isononanoate, and $C_{12}$ to $C_{15}$ alkyl benzoates;

$C_{12}$ to $C_{26}$ saturated fatty alcohols, such as, for example, octyldodecanol, isocetyl alcohol and behenyl alcohol;

fatty acids; and mixtures thereof.

The nonpolar oils can be chosen from, for example, silicone oils, such as, for example, volatile and nonvolatile and linear and cyclic polydimethylsiloxanes which are liquid at ambient temperature; and linear and branched hydrocarbons and fluorocarbons of synthetic or mineral origin, such as, for example, volatile paraffin oils (such as, for example, isoparaffins and isododecane) and nonvolatile paraffin oils and their derivatives, petrolatum, polydecenes, hydrogenated polyisobutene, such as, for example, parleam oil, and squalane.

According to certain embodiments of the present invention, the composition can comprise at least one oil chosen from esters of $C_8$–$C_{24}$ fatty acids and of polyols, and $C_{12}$ to $C_{26}$ saturated fatty alcohols, for example, octyldodecanol.

The fatty phase can also comprise other fatty substances, such as, for example, waxes, in so far as the latter are compatible with the other components of the composition and in so far as they do not detrimentally affect the properties of the composition, such as, for example, its transparency.

The composition of the present invention can additionally comprises any additive conventionally used in the field under consideration chosen from, for example, antioxidants, preservatives, neutralizing agents, cosmetic and dermatological active principles, such as, for example, emollients, moisturizing agents, vitamins, essential fatty acids, sunscreen agents, and their mixtures. When present in the composition of the invention, additives can be present in an amount ranging from 0.001 to 20%, for example from 0.01 to 10%, by weight with respect to the total weight of the composition. The composition can comprises, for example, at least one additive chosen from cosmetic and dermatological active principles.

Of course, a person skilled in the art will take care to choose the possible additional additives and/or their amount so that the advantageous properties of the composition according to the invention are not, or not substantially, detrimentally affected by the envisaged addition.

The present invention applies not only to scenting products but also to products for caring for, treating and making up the skin, including the scalp, and the lips comprising an odorous substance. The composition according to the present invention can thus be configured to be a composition for at least one of scenting, caring for, treating, and for making up keratinous substances and can be provided, for example, in the form of a transparent stick. It can constitute, for example, stick products for the antisun protection of the skin of the face; make-up removing products; products for making up the skin, both of the human face and the human body, in particular in the form of colored make-up products, such as foundations cast as a stick or in a dish, blushers and face powders, lipsticks, concealers and temporary tattooing products; products for making up the eyes, the eyebrows and/or the hair, such as eyeliners in the pencil form and mascara tablets; and body hygiene products. It can be, for example, used for scenting.

A further subject of the invention is a cosmetic process for the scenting of cosmetic substrates, including, for example, human keratinous substances, such as skin, lips and superficial body growths, comprising the application, to the cosmetic substrate, such as a keratinous substance, of the composition as defined herein.

According to certain embodiments of the present invention, the composition can comprise at least one coloring material which can be chosen from lipophilic dyes and hydrophilic dyes commonly used in any of cosmetic and dermatological compositions, and their mixtures. This coloring material can be present in an amount ranging from 0.001 to 5% of the total weight of the composition, for example 0.01 to 2% of the total weight of the composition.

The fat-soluble dyes are, for example, chosen from sudan red, DC Red 17, DC Green 6, β-carotene, soybean oil, sudan brown, DC Yellow 11, DC Violet 2, DC Orange 5, and quinoline yellow.

The composition according to the invention can be manufactured by known processes generally used in the cosmetic or dermatological field. It can be manufactured, for example, by the process comprising heating the polymer to at least its softening temperature, adding thereto the other components, optionally the at least one coloring material and optionally at least one additive, and mixing the combined mixture until a clear and transparent solution is obtained. The homogeneous mixture obtained can then be cast in an appropriate mold, such as, for example, a lipstick mould, or directly in the packaging articles (case, pot, and dish, for example).

The invention is illustrated in more detail in the following examples. The percentages are given by weight with respect to the total weight of the composition, unless otherwise mentioned.

EXAMPLE 1

Scenting Composition

| | |
|---|---|
| UNICLEAR 100 | 25% |
| Perfume extract | 4% |
| Perfume oil | 61% |
| Octyldodecanol | 10% |

Procedure: The constituents, except for the perfume extract, are mixed under hot conditions (approximately 80° C.) and the perfume extract is subsequently added. The mixture is stirred, then cast and allowed to cool to ambient temperature (20 to 25° C.).

A visually perfect transparent stick is obtained having a hardness with a strength of 73 g. This stick is highly scenting, the fragrance persisting for a long time after application to the skin.

Turbidity measurement: The measurement is carried out with the 2100P portable turbidimeter from Hach Company, the measuring tube being of the 2100P: AR397A, cat.24347-06 pk/6 type.

In order to carry out the measurement, the composition to be measured is cast in the measuring tube, which is placed in the turbidimeter. The turbidity value of this composition is 12.8 NTU.

Persistence Test

Comparative Test No. 1: the persistence of the stick of Example 1 according to the invention was measured with respect to a fluid composition comprising the same amount of perfume extract. The fluid composition is a commonly used scenting oil-in-water emulsion comprising 17% by weight of oils, 7% by weight of surfactants and cosurfactants, 4% by weight of perfume extract and 7% by weight of glycerol, the remainder to 100% by weight being water.

In order to measure the persistence of the compositions studied, approximately 25 mg of the composition is placed in a 4 ml vial (small screw-capped and crimped bottle), having a contact area of 40 mm$^2$, in dynamic evaporative equilibrium under a flow of 45 ml of air per minute and at a temperature of 40° C. On 6 specific occasions, ranging from 5 minutes to 6 h 10 minutes after the application of the composition, the amount of fragrance released by the residual fragrance in the composition studied is quantified.

The values in the following Table (1), expressed in integration units (IU×10$^{-5}$), represent the sum of the areas of the peaks of the fragrance on each occasion in the quantifying.

TABLE 1

| Composition | Measurement at 5 min | Measurement at 45 min | Measurement at 1 h 33 min | Measurement at 2 h 15 min | Measurement at 4 h 12 min | Measurement at 6 h 10 min |
|---|---|---|---|---|---|---|
| Stick of Example 1 | 13.15 | 5.64 | 3.78 | 3.12 | 1.73 | 0.87 |
| Fluid | 16.32 | 3.10 | 1.61 | 1.20 | 0.49 | 0.44 |

This table demonstrates that, after 6 hours of controlled dynamic evaporation, the anhydrous stick according to the invention releases twice as much fragrance as the fluid composition of the prior art and that the amount of fragrance released by the stick after 4 hours 12 minutes is equivalent to that released by the fluid composition after 1 hour 33 minutes. Thus, the persistence effect of the sticks according to the invention is approximately three times greater than that of the fluid composition which is compared with it.

Comparative Test No. 2: the persistence of the stick of Example 1 according to the invention in which the perfume extract was limonene or citronellol was measured, according to the same test as above, with respect to a solid composition of the prior art comprising the same amount of the same perfume extract. The solid composition of the prior art comprises 53.4% by weight of hydrocarbonaceous oil, 9% by weight of waxes, 4% by weight of perfume extract, 33.5% by weight of fillers and 0.1% by weight of dyes and antioxidants.

The values in the following Tables (2) and (3), expressed in integration units (IU×10$^{-3}$), represent the sum of the areas of the peaks of the fragrance on each occasion in the quantifying for limonene (Table 2) and citronellol (Table 3).

TABLE 2

| Composition with limonene | Measurement at 10 min | Measurement at 1 h | Measurement at 1 h 50 min | Measurement at 3 h | Measurement at 4 h 30 min | Measurement at 6 h |
|---|---|---|---|---|---|---|
| Solid composition of the prior art | 18.8 | 6.3 | 3.1 | 1.1 | 0.28 | 0 |
| Stick of Example 1 | 10.9 | 5.9 | 3.8 | 2 | 0.9 | 0.4 |

TABLE 3

| Composition with citronellol | Measurement at 10 min | Measurement at 1 h | Measurement at 1 h 50 min | Measurement at 3 h | Measurement at 4 h 30 min | Measurement at 6 h |
|---|---|---|---|---|---|---|
| Solid composition of the prior art | 18.9 | 9.7 | 6 | 2.8 | 1.09 | 0.53 |
| Stick of Example 1 | 8.1 | 5.8 | 4.6 | 3.3 | 2.2 | 1.6 |

Tables (2) and (3) show that the stick according to the invention makes possible a more gradual and more enduring release of the fragrance and thus better persistence over time.

EXAMPLE 2

Balm for the Lips Scented with Violet

| UNICLEAR 100 | 25% |
|---|---|
| "Violine" fragrance | 4% |
| Parleam oil | 60.998% |
| Octyldodecanol | 10% |
| D&C Violet No. 2 dye | 0.002% |

The procedure used to prepare this example is the same as in Example 1.

A stick balm for the lips is obtained which is perfectly transparent, which is colored violet and which pleasantly scents the lips. This stick has a hardness with a strength of 47 g.

The turbidity measurement is carried out in the same way as in Example 1. A turbidity value of 12.8 NTU is obtained.

EXAMPLE 3

Scenting Stick

| VERSAMID 940 | 25% |
|---|---|
| Fragrance | 2% |
| Octyldodecanol | 73% |

The procedure used to prepare this example is the same as in Example 1.

A visually perfect transparent stick is obtained with a hardness with a strength of 52.5 g.

The turbidity measurement is carried out in the same way as in Example 1. The turbidity value of 18.6 NTU is obtained.

EXAMPLE 4

Scenting Cast Product

| CASAMID 872 | 25% |
|---|---|
| Fragrance | 2% |
| Octyldodecanol | 73% |

The procedure used to prepare this example is the same as in Example 1.

A transparent soft cast product is obtained which is presented in dishes and which has a hardness with a strength of 5 g.

The turbidity measurement is carried out in the same way as in Example 1. A turbidity value of 334 NTU is obtained.

EXAMPLE 5

Scenting Cast Product

| UNI-REZ 100 | 20% |
|---|---|
| Fragrance | 2% |
| Octyldodecanol | 78% |

The procedure used in this example is the same as in Example 1.

A transparent soft product is obtained which is presented in dishes and which has a hardness with a strength of 6 g. The turbidity measurement is carried out in the same way as in Example 1. A turbidity value of 7.98 NTU is obtained.

What is claimed is:

1. A product comprising:

a transparent anhydrous solid composition cosmetic composition comprising a physiologically acceptable medium, wherein said physiologically acceptable medium comprises at least one odorous substance in an amount of at least 2% by weight with respect to a total weight of the composition; and a liquid fatty phase comprising at least one polymer, wherein said at least one polymer has a weight-average molecular mass ranging from 1,000 to 30,000, and comprises a) a polymer backbone comprising hydrocarbonaceous repeat units comprising at least one heteroatom and b) at least one fatty chain chosen from pendant and end fatty chains, wherein said at least one fatty chain is optionally functionalised; comprises from 12 to 120 carbon atoms; and is bonded to at least one of the hydrocarbonaceous repeat units.

2. The product according to claim 1, wherein the liquid fatty phase comprises at least one polar oil and at least one nonpolar oil.

3. The product according to claim 1, wherein said composition comprises at least one oil chosen from esters of $C_8$–$C_{24}$ fatty acids and of at least one source of —OH chosen from polyols and $C_{12}$ to $C_{26}$ saturated fatty alcohols.

4. The product according to claim 1, wherein said composition comprises octyldodecanol.

5. The product according to claim 1, wherein at least one of the hydrocarbonaceous repeat units comprises at least one amide.

6. The product according to claim 1, wherein the at least one polymer comprises the at least one fatty chain in an amount ranging from 40 to 98% of a total number of the repeat units with a heteroatom and of the at least one fatty chain.

7. The product according to claim 1, wherein the at least one polymer comprises the at least one fatty chain in an amount ranging from 50 to 95% of a total number of the repeat units with a heteroatom and of the at least one fatty chain.

8. The product according to claim 1, wherein the at least one fatty chain is bonded directly to at least one heteroatom in the polymer backbone.

9. The product according to claim 1, wherein said at least one fatty chain comprises from 12 to 68 carbon atoms.

10. The composition according claim 1, wherein the at least one polymer has a weight-average molecular mass ranging from 2,000 to 20,000.

11. The composition according to claim 1, wherein the at least one polymer has a weight-average molecular mass ranging from 2,000 to 10,000.

12. The product according to claim 1, wherein the at least one polymer comprises at least one polymer of formula (I):

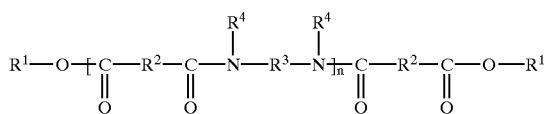

(I)

wherein n denotes a whole number of amide units, with the proviso that that the polymer of formula (I) comprises ester groups in an amount ranging from 10 to 50% of a total number of ester and amide groups;

each $R^1$ is, independently, chosen from alkyl and alkenyl groups comprising at least 4 carbon atoms;

each $R^2$ is, independently, chosen from $C_4$ to $C_{42}$ hydrocarbonaceous groups, with the proviso that at least 50% of the $R^2$ groups are chosen from $C_{30}$ to $C_{42}$ hydrocarbonaceous group;

each $R^3$ is, independently, chosen from organic groups comprising at least 2 carbon atoms, at least one hydrogen atom, and optionally at least one atom chosen from oxygen and nitrogen atoms; and each $R^4$ is, independently, chosen from a hydrogen atom, $C_1$ to $C_{10}$ alkyl groups, and a direct bond to one of $R^3$ and another $R^4$ such that the nitrogen atom to which both $R^3$ and $R^4$ are bonded forms part of a heterocyclic structure defined by $R^4$—N—$R^3$, with the proviso that at least 50% of the $R^4$ groups are chosen from a hydrogen atom.

13. The composition according claim 12, wherein each $R^1$ is, independently, chosen from $C_{12}$ to $C_{22}$ alkyl groups.

14. The product according to claim 12, wherein each $R^2$ is, independently, chosen from groups comprising from 30 to 42 carbon atoms.

15. The product according to claim 1, wherein the at least one polymer is chosen from copolymers of a $C_{36}$ diacid condensed with ethylenediamine, wherein said copolymers are esterified with at least one of cetylstearyl alcohol and stearyl alcohol; polyamide resins resulting from the condensation of an aliphatic dicarboxylic acid and of a diamine, wherein carbonyl and amine groups of adjacent individual units are condensed via an amide bond; polyamides of fatty acid dimers and of aliphatic diamines; and polyamides comprising dimeric fatty acids.

16. The product according to claim 1, wherein the composition comprises the at least one polymer in an amount ranging from 0.5 to 50% of the total weight of the composition.

17. The product according to claim 1, wherein the composition comprises the at least one polymer in an amount ranging from 5 to 40% of the total weight of the composition.

18. The product according to claim 1, wherein the at least one odorous substance comprises at least one of a fragrance and an aroma of natural and synthetic origins, and mixtures thereof.

19. The product according to claim 1, wherein the composition comprises the at least one odorous substance in an amount ranging from 2 to 15% by weight with respect to the total weight of the composition.

20. The product according to claim 1, wherein the composition comprises the at least one odorous substance in an amount ranging from 3 to 12% with respect to the total weight of the composition.

21. The composition according claim 1, wherein the composition comprises the liquid fatty phase in an amount of at least 20% by weight with respect to a total weight of the composition.

22. The product according to claim 1, wherein the composition comprises the liquid fatty phase in an amount ranging from 20 to 88.5% by weight with respect to the total weight of the composition.

23. The product according to claim 1, wherein said cosmetic composition is configured for at least one of scenting, caring for, treating, and making up keratinous substances.

24. The product according to claim 1, wherein said composition has a hardness with a strength ranging from 5 to 600 grams.

25. The product according to claim 1, wherein said product comprises one of a transparent stick and a cast product.

26. The product according to claim 1, wherein said cosmetic composition is configured as a cosmetic scenting product.

27. The product according to claim 1, wherein said cosmetic composition is colored.

28. The product according to claim 1, wherein said cosmetic composition comprises at least one particulate component.

29. A cosmetic process for the scenting of the keratinous substances of human beings, comprising applying to a keratinous substances a product comprising a transparent anhydrous solid composition cosmetic composition comprising a physiologically acceptable medium, wherein said physiologically acceptable medium comprises at least one odorous substance in an amount of at least 2% by weight with respect to a total weight of the composition; and a liquid fatty phase comprising at least one polymer, wherein said at least one polymer has a weight-average molecular mass ranging from 1,000 to 30,000, and comprises a) a polymer backbone comprising hydrocarbonaceous repeat units comprising at least one heteroatom and b) at least one fatty chain chosen from pendant and end fatty chains, wherein said at least one fatty chain is optionally functionalised; comprises from 12 to 120 carbon atoms; and is bonded to at least one of the hydrocarbonaceous repeat units.

30. A product comprising:

a transparent anhydrous solid composition cosmetic composition comprising a physiologically acceptable medium, wherein said physiologically acceptable medium comprises at least one odorous substance in an amount of at least 2% by weight; and a liquid fatty phase comprising at least one polyamide, wherein said at least one polyamide has a weight-average molecular mass ranging from 1,000 to 30,000, and comprises a) a polymer backbone comprising amide repeat units and b) optionally at least one fatty chain chosen from pendant and end fatty chains, wherein said at least one fatty chain is optionally functionalised; comprises from 12 to 120 carbon atoms; and is bonded to at least one of the amide units.

31. The product according to claim 30, wherein the liquid fatty phase comprises at least one polar oil and at least one nonpolar oil.

32. The product according to claim 30, wherein said composition comprises at least one oil chosen from esters of $C_8$–$C_{24}$ fatty acids and of at least one source of —OH chosen from polyols and $C_{12}$ to $C_{26}$ saturated fatty alcohols.

33. The product according to claim 30, wherein said composition comprises octyldodecanol.

34. The product according to claim 30, wherein the at least one polyamide comprises at least one pendant fatty chain bonded directly to at least one nitrogen atom of the amide repeat units.

35. The product according to claim 30, wherein the at least one polyamide comprises at least one end fatty chain bonded to the polymer backbone via at least one ester group.

36. The product according to claim 30, wherein the at least one polyamide comprises the at least one fatty chain in an amount ranging from 40 to 98% of a total number of the amide units and of the at least one fatty chain.

37. The composition according claim 30, wherein the at least one polyamide comprises the at least one fatty chain in an amount ranging from 50 to 95% of a total number of the amide units and of the at least one fatty chain.

38. The product according to claim 30, wherein the at least one polyamide comprises said at least one fatty chain and said at least one fatty chain comprises from 12 to 68 carbon atoms.

39. The composition according claim 30, wherein the at least one polyamide has a weight-average molecular mass ranging from 2,000 to 20,000.

40. The composition according claim 30, wherein the at least one polyamide has a weight-average molecular mass ranging from 2,000 to 10,000.

41. The product according to claim 30, wherein the at least one polyamide is chosen from polyamide of formula (I):

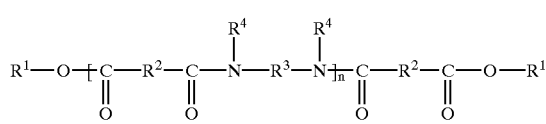

wherein n denotes a whole number of amide units, with the proviso that that the polymer of formula (I) comprises ester groups in an amount ranging from 10 to 50% of a total number of ester and amide groups;

each $R^1$ is, independently, chosen from alkyl and alkenyl groups comprising at least 4 carbon atoms;

each $R^2$ is, independently, chosen from $C_4$ to $C_{42}$ hydrocarbonaceous groups, with the proviso that at least 50% of the $R^2$ groups are chosen from $C_{30}$ to $C_{42}$ hydrocarbonaceous group;

each $R^3$ is, independently, chosen from organic groups comprising at least 2 carbon atoms, at least one hydrogen atom, and optionally at least one atom chosen from oxygen and nitrogen atoms; and each $R^4$ is, independently, chosen from a hydrogen atom, $C_1$ to $C_{10}$ alkyl groups, and a direct bond to one of $R^3$ and another $R^4$ such that the nitrogen atom to which both $R^3$ and $R^4$ are bonded forms part of a heterocyclic structure defined by $R^4$—N—$R^3$, with the proviso that at least 50% of the $R^4$ groups are chosen from a hydrogen atom.

42. The composition according claim 41, wherein each $R^1$ is, independently, chosen from $C_{12}$ to $C_{22}$ alkyl groups.

43. The product according to claim 41, wherein each $R^2$ is, independently, chosen from groups comprising from 30 to 42 carbon atoms.

44. The product according to claim 30, wherein the composition comprises the at least one polyamide in an amount ranging from 0.5 to 50% of the total weight of the composition.

45. The product according to claim 30, wherein the composition comprises the at least one polyamide in an amount ranging from 5 to 40% of the total weight of the composition.

46. The product according to claim 30, wherein the at least one odorous substance comprises at least one of a fragrance and an aroma of natural and synthetic origins, and mixtures thereof.

47. The product according to claim 30, wherein the composition comprises the at least one odorous substance in an amount ranging from 2 to 15% by weight with respect to the total weight of the composition.

48. The product according to claim 30, wherein the composition comprises the at least one odorous substance in an amount ranging from 3 to 12% with respect to the total weight of the composition.

49. The product according claim 30, wherein the composition comprises the liquid fatty phase in an amount of at least 20% by weight with respect to a total weight of the composition.

50. The product according to claim 30, wherein the composition comprises the liquid fatty phase in an amount ranging from 20 to 88.5% by weight with respect to the total weight of the composition.

51. The product according to claim 30, wherein said cosmetic composition is configured for at least one of scenting, caring for, treating, and making up keratinous substances.

52. The product according to claim 30, wherein said composition has a hardness with a strength ranging from 5 to 600 grams.

53. The product according to claim 30, wherein said cosmetic composition comprises one of a transparent stick and a cast product.

54. The product according to claim 30, wherein said cosmetic composition is configured as a cosmetic scenting product.

55. The product according to claim 30, wherein said cosmetic composition is colored.

56. The product according to claim 30, wherein said cosmetic composition comprises at least one particulate component.

57. A cosmetic process for the scenting of the keratinous substances of human beings, comprising applying to a keratinous substances a product comprising a transparent anhydrous solid composition cosmetic composition comprising a physiologically acceptable medium, wherein said physiologically acceptable medium comprises at least one odorous substance in an amount of at least 2% by weight; and a liquid fatty phase comprising at least one polyamide, wherein said at least one polyamide has a weight-average molecular mass ranging from 1,000 to 30,000, and comprises a) a polymer backbone comprising amide repeat units and b) optionally at least one fatty chain chosen from pendant and end fatty chains, wherein said at least one fatty chain is optionally functionalised; comprises from 12 to 120 carbon atoms; and is bonded to at least one of the amide units.

58. A method of controlling a persistence of at least one odorous substance on a cosmetic substrate comprising:

incorporating the at least one odorous substance in a cosmetic composition comprising a physiologically acceptable medium comprising at least one polymer in an amount effective for controlling the persistence of the at least one odorous substance, wherein said at least one polymer has a weight-average molecular mass ranging from 1,000 to 30,000; and comprises a) a polymer backbone comprising hydrocarbonaceous repeat units comprising at least one heteroatom and b) at least one fatty chain chosen from pendant and end fatty chains, wherein said fatty chains are optionally functionalised, comprise from 12 to 120 carbon atoms, and are bonded to the hydrocarbonaceous repeat units; and applying said cosmetic composition to said cosmetic substrate.

59. The method according to claim 58, wherein said at least one polymer is chosen from polymers of formula (I):

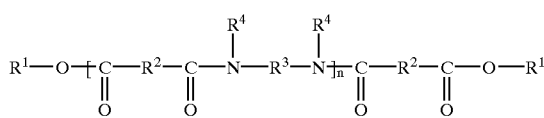

(I)

wherein n denotes a whole number of amide units, with the proviso that that the polymer of formula (I) comprises ester groups in an amount ranging from 10 to 50% of a total number of ester and amide groups;

each $R^1$ is, independently, chosen from alkyl and alkenyl groups comprising at least 4 carbon atoms;

each $R^2$ is, independently, chosen from $C_4$ to $C_{42}$ hydrocarbonaceous groups, with the proviso that at least 50% of the $R^2$ groups are chosen from $C_{30}$ to $C_{42}$ hydrocarbonaceous group;

each $R^3$ is, independently, chosen from organic groups comprising at least 2 carbon atoms, at least one hydrogen atom, and optionally at least one atom chosen from oxygen and nitrogen atoms; and each $R^4$ is, independently, chosen from a hydrogen atom, $C_1$ to $C_{10}$ alkyl groups, and a direct bond to one of $R^3$ and another $R^4$ such that the nitrogen atom to which both $R^3$ and $R^4$ are bonded forms part of a heterocyclic structure defined by $R^4$—N—$R^3$, with the proviso that at least 50% of the $R^4$ groups are chosen from a hydrogen atom.

60. The method according to claim 58, wherein said controlling comprises enhancing the persistence of the least one odorous substance on the cosmetic substrate.

61. A method of controlling a persistence of at least one odorous substance on a cosmetic substrate comprising incorporating the at least one odorous substance in a cosmetic composition comprising a physiologically acceptable medium comprising at least one polyamide in an amount effective for controlling the persistence of the at least one odorous substance, wherein said at least one polyamide has a weight-average molecular mass ranging from 1,000 to 30,000, and comprises a) a polymer backbone comprising amide repeat units and b) optionally at least one fatty chain chosen from pendant and end fatty chains, wherein said pendant and end fatty chains are optionally functionalized pendant, comprise from 12 to 120 carbon atoms which, and are bonded to the amide units; and applying said cosmetic composition to said cosmetic substrate.

62. The method according to claim 61, wherein said at least one polymer is chosen from polymers of formula (I):

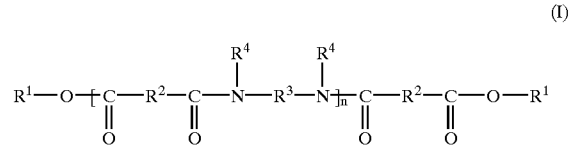

(I)

wherein n denotes a whole number of amide units, with the proviso that that the polymer of formula (I) comprises ester groups in an amount ranging from 10 to 50% of a total number of ester and amide groups;

each $R^1$ is, independently, chosen from alkyl and alkenyl groups comprising at least 4 carbon atoms;

each $R^2$ is, independently, chosen from $C_4$ to $C_{42}$ hydrocarbonaceous groups, with the proviso that at least 50% of the $R^2$ groups are chosen from $C_{30}$ to $C_{42}$ hydrocarbonaceous group;

each $R^3$ is, independently, chosen from organic groups comprising at least 2 carbon atoms, at least one hydrogen atom, and optionally at least one atom chosen from oxygen and nitrogen atoms; and each $R^4$ is, independently, chosen from a hydrogen atom, $C_1$ to $C_{10}$ alkyl groups, and a direct bond to one of $R^3$ and another $R^4$ such that the nitrogen atom to which both $R^3$ and $R^4$ are bonded forms part of a heterocyclic structure defined by $R^4$—N—$R^3$, with the proviso that at least 50% of the $R^4$ groups are chosen from a hydrogen atom.

63. The method according to claim 61, wherein said controlling comprises enhancing the persistence of the least one odorous substance on the cosmetic substrate.

\* \* \* \* \*

UNITED STATES PATENT AND TRADEMARK OFFICE
CERTIFICATE OF CORRECTION

PATENT NO.   : 6,432,391 B1
DATED        : August 13, 2002
INVENTOR(S)  : Isabelle Bara It is certified that error appears in the above-identified patent and that said Letters Patent is hereby corrected as shown below:

<u>Column 14,</u>
Line 60 and 63, after "according" insert -- to --.

<u>Column 15,</u>
Line 10, after "proviso" delete "that" (second occurrence).
Line 19, "group" should read -- groups --.
Lines 31 and 66, after "according" insert -- to --.

<u>Column 16,</u>
Line 27, "keratinous substances" should read -- keratinous substance --.

<u>Column 17,</u>
Lines 13, 21 and 24, after "according" insert -- to --.
Line 38, after "proviso" delete "that" (second occurrence).
Line 47, "group" should read -- groups --.
Line 59, after "according" insert -- to --.

<u>Column 18,</u>
Line 17, after "according" insert -- to --.
Line 45, "keratinous substances" should read -- keratinous substance --.

<u>Column 19,</u>
Line 22, after "proviso" delete "that" (second occurrence).
Line 30, "group" should read -- groups --.
Line 44, before "least" insert -- at --.

UNITED STATES PATENT AND TRADEMARK OFFICE
CERTIFICATE OF CORRECTION

PATENT NO. : 6,432,391 B1
DATED : August 13, 2002
INVENTOR(S) : Isabelle Bara

It is certified that error appears in the above-identified patent and that said Letters Patent is hereby corrected as shown below:

<u>Column 20,</u>
Line 9, after "atoms" delete "which".
Line 25, after "proviso" delete "that" (second occurrence).
Line 34, "group" should read -- groups --.
Line 41, "$R^4$such" should read -- $R^4$ such --.
Line 47, before "least" insert -- at --.

Signed and Sealed this

Twenty-first Day of January, 2003

JAMES E. ROGAN
*Director of the United States Patent and Trademark Office*